United States Patent [19]

Shastri et al.

[11] 4,017,615

[45] Apr. 12, 1977

[54] PROPYLENE CARBONATE OINTMENT VEHICLE

[75] Inventors: Subramaniam Shastri, Cupertino; Zafaruzzaman I. Shaikh, Palo Alto, both of Calif.

[73] Assignee: Syntex Corporation, Panama, Panama

[22] Filed: Dec. 11, 1975

[21] Appl. No.: 639,740

Related U.S. Application Data

[62] Division of Ser. No. 85,246, Oct. 29, 1970, abandoned.

[52] U.S. Cl. .............................. 424/241; 424/242; 424/243
[51] Int. Cl.$^2$ ........................................ A61K 31/58
[58] Field of Search ................... 424/241, 242, 243

[56] References Cited

UNITED STATES PATENTS

| | | | |
|---|---|---|---|
| 3,136,696 | 6/1964 | Harrison | 424/73 |
| 3,178,352 | 4/1965 | Ericksun | 424/73 |
| 3,185,627 | 5/1965 | Kass | 424/73 X |
| 3,592,930 | 7/1971 | Katz | 424/243 |
| 3,924,004 | 12/1975 | Chang et al. | 424/243 |

FOREIGN PATENTS OR APPLICATIONS

| | | |
|---|---|---|
| 1,448,042 | 6/1966 | France |
| 1,096,753 | 12/1967 | United Kingdom |

Primary Examiner—Elbert L. Roberts
Attorney, Agent, or Firm—Tom M. Moran; Joseph I. Hirsch

[57] ABSTRACT

An ointment vehicle containing from 0.5 to 30 percent propylene carbonate, from 30 to 99.5 weight percent petrolatum and/or polysiloxane, compatible cosolvent, the concentration of which in combination with propylene carbonate is from 0.5 to 70 percent, and, optionally, surfactants, thickeners, preservatives, and penetrants. This ointment is a suitable vehicle for all types of therapeutic agents for topical application including antibiotics, steroids, antihistamines, antiseptics, anesthetics, antibacterials, fungicides and the like, and has shown particular advantages with anti-inflammatory topical corticoids.

7 Claims, No Drawings

PROPYLENE CARBONATE OINTMENT VEHICLE

This is a division of application U.S. Ser. No. 85,246 filed Oct. 29, 1970, now abandoned.

This invention relates to ointment bases for topical application of medicaments and to mixtures of the ointment bases and medicaments. In particular, this invention relates to new, improved ointment bases having advantages over previously known ointment bases.

One of the oldest type of medicament vehicles is the ointment, a semi-solid preparation containing active medications which can be readily spread on and rubbed into the skin. It serves as a means for distributing the medication uniformly over the skin surface and maintaining it there until beneficial action can occur. Previously known ointment preparations were based primarily on fats, greases and petrolatum. Medicaments generally have a very slight solubility in the petrolatum and are distributed in the petrolatum as finely divided particles. The efficacy of such preparations was insufficient, and creams and solutions were developed in an attempt to improve medicament efficacy. However, the creams and solutions were not occlusive and could not induce hydration of the stratum corneum, an effect much desired in treatment of certain conditions.

It is the object of this invention to provide an ointment base having greatly enhanced efficacy. This improvement is obtained by the use of propylene carbonate in the ointment base composition.

The ointment vehicle according to this invention can have the composition shown in Table A.

| Ingredient | Concentration, Wt.% Operable | Concentration, Wt.% Preferred |
|---|---|---|
| Propylene carbonate | 0.1 – 30 | 0.1 – 30 |
| Petrolatum and/or polysiloxane | 30 – 99.5 | 60 – 95 |
| Cosolvent | (a) | (a) |
| Surfactant | 0 – 45 | 0 – 15 |
| Thickener | 0 – 20 | 0 – 10 |
| Penetrant | 0 – 25 | 0 – 10 |

(a)The combined concentration of cosolvent and propylene carbonate is from 0.5 to 70 and preferably from 0.5 to 35 weight percent of the ointment base.

All concentrations are herein given as weight percents unless otherwise specified. It is also intended that the chemical compounds in each class of ingredients described herein be limited to pharmaceutically acceptable compounds in the concentrations indicated.

The petrolatum component in the ointment of this invention can be any paraffin ranging in viscosity from mineral oil to paraffin waxes. The preferred petrolatums are paraffin having the consistency of petrolatum NF (petroleum jelly).

The polysiloxanes (also known as silicones) suitable for use in the ointment of this invention have a viscosity in the range of from 0.5 to $10^6$ centistokes. The organic moieties attached to the polysiloxane are preferably lower molecular weight hydrocarbon moieties, having from 1 to 8 carbons, such as lower alkyl, lower alkenyl, phenyl and alkyl substituted phenyl, and phenylalkyl such as benzyl. The preferred hydrocarbon moieties are alkyl groups having from 1 to 3 carbons such as dimethylsiloxane polymer.

The compatible cosolvents in the ointment of this invention are pharmaceutically acceptable compounds which function as cosolvents and/or coupling agents for the propylene carbonate and petrolatum or polysiloxane. The cosolvent also maintain homogeneity of the vehicle and prevent exudation of "bleeding" of the propylene carbonate from the mixture. Examples of suitable cosolvents include the following:

A. Monohydric alcohols having from 1 to 22 carbons such as methanol, ethanol, propanol, isopropanol, butanol, hexanol, cetyl alcohol, stearyl alcohol, and the like.

B. Dihydric and polyhydric alcohols having from 2 to 22 carbons such as propylene glycol, glycerin, hexanetriols such as 1,2,6-hexanetriol, sorbitol, 1,3-butanediol, 2,3-butanediol, etc.

C. Lower alkyl ethers of glycols having from 1 to 6 carbons such as the monomethyl or monoethyl ether of ethylene or diethylene or propylene or dipropylene glycol, Ucars (propylene glycol or dipropylene glycol monomethyl ethers), Carbitols (diethylene glycol monoethyl ether), Cellosolve (ethylene glycol monomethyl ether), etc.

D. Polyethylene glycols and polypropylene glycols having molecular weights of from 100 to 20,000.

E. Esters of aliphatic monobasic and dibasic acids having from 2 to 22 carbons and monohydric alcohols having from 1 to 20 carbons, di- and polyhydric alcohols having from 2 to 20 carbons, and sugar alcohols such as isopropyl myristate, myristyl myristate, cetyl stearate, methyl stearate, isopropyl sebacate, methyl sebacate, sucrose monolaurate, sucrose monostearate, etc.

F. Sterols such as cholestrol, etc.

The ointment of this invention can also contain one or more surfactants. Suitable surfactants include anionic, cationic, amphoteric and nonionic surfactants which are pharmaceutically acceptable in topical applications. Any one or more surfactants having the above characteristics can be used. Representative examples of suitable surfactants which can be used in the ointment base of this invention are described in *Remington's Practice of Pharmacy* by Martin and Cook, 12th edition, 1961, pages 219–226, *Cosmetics; Their Principles and Practices* by R.G. Harry, 1965, pages 396–398 and 413–417, and *Cosmetics Science and Technology* by E. Sagarin, 1957, pages 328–333, 1060–1063 and 1254, which publications are herein incorporated by reference. Representative surfactants which are suitable include:

A. Anionic agents
1. Sodium, potassium and ammonium soaps derived from fatty acids having from 10 to 22 carbon atoms; and polyvalent metal (magnesium, calcium, zinc, aluminum and lead) soaps derived from fatty acids having from 10 to 22 carbons.
2. Amine soaps derived from fatty acids having from 10 to 22 carbons and primary, secondary and tertiary amines such as monoethanolamine, diethanolamine and triethanolamine, and cyclic amines such as morpholine, e.g., triethanolamine stearate.
3. Rosin soaps such as sodium salts of rosin acids such as abietic acid.
4. Alkali metal salts of sulfate compounds which can be represented by the formula $ROSO_3H$ wherein the R group represents an organic moiety such as a fatty alcohol having up to 22 carbons, e.g., sodium lauryl sulfate, sodium cetyl sulfate, sodium monolauryl glyceryl sulfate, an oil such as sulfated castor, olive, teaseed, neat's foot cottonseed, rape seed, corn and rice, oil, etc.

5. Alkali metal salts of sulfonated compounds which can be represented by the formula $RSO_3H$ wherein the R group can have from 8 to 22 carbons. These include alkane sulfonates such as dioctyl sodium sulfosuccinate, oxyethylated alkylaryl sulfate; alkyl aromatic sulfonates such as sodium isopropylnaphthalenesulfonate, sodium dodecylbenzenesulfonate, sodium sulfonaphthylstearate.

B. Cationic agents

1. Amine salts (e.g. hydrochlorides and acetates) derived from straight chain fatty amines having from 8 to 18 carbons, e.g., octodecylamine hydrochloride.
2. Quaternary ammonium salts formed by alkylation of fatty amines with methyl chloride, dimethylsulfate, benzylchloride and the like. These compounds can be represented by the formula [RR'R'' R'''N]Y wherein each of R, R', R'', R''' is a long chain aliphatic group of from 8 to 22 carbons or a fatty acid amide; short aliphatic group such as methyl, ethyl, or propyl, an aromatic group such as a phenyl or benzyl radical; or a heterocyclic group such as pyridine or piperidine; and Y represents an inorganic or lower organic ion such as chloride, bromide or acetate radical, e.g., triethanolamine stearate, cetyl trimethyl ammonium bromide, benzalkoniumchloride.

C. Nonionic

1. Ethers such as condensation products of alkylphenols with from 6 to 20 moles of ethylene oxide, the phenols being monoalkylated, dialkylated or polyalkylated with alkyl side chains having from 5 to 18 carbons and the corresponding napththalene or diphenyl compounds; polyoxyethylene and polyoxyethylene-polyoxypropylene copolymers.
2. Esters such as compounds which can be represented by the formula RCOOR' wherein R is a long hydrocarbon chain derived from a fatty acid having from 12 to 22 carbons and R' is a polyhydric alcohol, e.g., glyceryl monostearate, diethylene glycol monolaurate, sorbitan fatty acid esters derived, for example from lauric, palmitic, stearic and oleic acids.
3. Ether-esters wherein polyoxyethylene chains are found with an unreacted hydroxy group of esters of fatty acids and polyhydric alcohols.
4. Fatty acid amides such as lauroyl diethanolamide.

D. Ampholytic

1. Surfactants such as those having amino and carboxy groups, e.g., dodecyl β-alanine, imidazoline derivatives such as Miranols.
2. Surfactants containing amino and sulfuric acid or sulfonic groups formed by condensing an alkanesulfonamide with formaldehyde and methyltaurine.

Suitable representative surfactants include sorbitan trioleate, sorbitan tristearate, sorbitan sesquioleate, glycerol monostearate, sorbitan monostearate, sorbitan monopalmitate, sorbitan monolaurate, polyoxyethylene lauryl ether, polyethylene glycol 400 monostearate, triethanolamine oleate, polyoxyethylene glycol 400 monolaurate, polyoxyethylene sorbitan monostearate, polyoxyethylenesorbitan monooleate, polyoxyethylene sorbitan monolaurate, sodium oleate, potassium oleate, sodium lauryl sulfate, lauroyl imidazoline, sodium dodecylbenzene sulfonate, sodium monoglyceride sulfate, sodium alkaralkyl polyglycol sulfate, sodium oleyl taurate, sodium dioctyl sulfosuccinate, lauryl polyglycol, ether, sodium dibutylnapthalenesulfonate, alkyl phenol polyglycol ether, sorbitan monolaurate polyglycol ether, sulfonated castor oil, tall oil polyglycol ester, alkyl dimethyl benzylammonium chloride alkyl naphthalene pyridinium chloride, cetyl dimethyl ethylammonium bromide, alkyl dimethyl chlorobenzylammonium chloride, dibutyl phenyl phenol sulfoate, ester of colaminoethylformyl methyl pyridinium chloride, sulfonated methyl oleylamide, sorbitan monolaurate polyglycol ether, polyglycol oleate, sodium lauryl sulfoacetate, sodium 2-ethylhexanol sulfate, sodium 7-ethyl-2-methylundecanol-4 sulfate, sodium 3,9-diethyltridecanol-6 sulfate, sodium lauryl and myristyl collamide sulfonate and N-(sodium sulfoethyl)oleamide, etc.

Suitable thickeners for use in the composition of this invention include colloidal alumina, colloidal silica, alginic acid and derivatives thereof, Carbopol (carboxyvinyl polymer), cellulose derivatives such as Klucel (cellulose ethers), Methocel (methyl cellulose), Natrosol (hydroxyethyl cellulose), sodium carboxymethyl cellulose, gelatin, gums such as agar, tragacanth, acacia gum, guar gum, and the like and egg yolk, lecithin, pectin, thixcin, and resins like ethyleneoxide polymers.

Other adjuvants which can be incorporated in the composition of this invention include waxes such as beeswax, spermaceti, paraffin waxes, and fatty acids, alcohols and amides having from 10 to 22 carbons.

The penetrants which can be used in the ointment base of this invention include dialkyl sulfoxide having up to 22 carbons in each alkyl group, e.g., dimethylsulfoxide, dimethylformamide, dimethylacetamide, tetrahydrofuran, and tetrahydrofurfuryl alcohol. The ointment can also contain penetration aids such as hydrocarbons such as squalene and squalane, acetylated lanolin fractions, etc., and the like.

The ointment base of this invention can also contain suitable preservatives or inhibitors such as methyl, ethyl, propyl, and butyl esters of parahydroxybenzoic acid, propyl gallate, sorbic acid and its sodium and potassium salts, propionic acid and its calcium and sodium salts, Dioxin (6-acetoxy-2,4-dimethyl-m-dioxane), Bronopol (2-bromo-2-nitropropane-1,3-diol), and salicylanilides such as dibromosalicylanilide, tribromosalicylamilides, Cinaryl 100 and 200 or Dowicil 100 and 200 (Cis isomer of 1-(3-chloroallyl-3,5,7-triaza-1-azanidadamantane chloride), hexachlorophene, sodium benzoate, citric acid, ethylene diamide-tetraacetic acid and its alkali metal and alkaline earth metal salts, butyl hydroxyanisol, butyl hydroxytoluene, phenolic compounds such as chloro- and bromocresols and chloro- and bromo- oxylenols, quaternary ammonium compounds like benzalkonium chloride, aromatic alcohols such as phenylethyl alcohol, benzyl alcohol, etc., chlorobutanol, and quinoline derivatives such as iodochlorhydroxyquinolin, etc.

The ointment of this invention can be made from the above ingredients by thoroughly mixing them at ambient or elevated temperatures. Preferably the components are thoroughly mixed while each is in a liquid state, and the mixture is cooled with good agitation to room temperature. Additional mechanical agitation and/or shock cooling steps can be used as intermediate or final steps in the manufacturing process to impart more homogeneity or improve texture. Process equipment suitable for these steps is known and includes heat exchangers, propeller mixers, colloid mills, homogenizers, roller mills sonic mixers and the like.

The ointment base of this invention can be used successfully as a vehicle for all types of therapeutic agents for topical application including antibiotics such as oxytetracycline, chlorotetracycline, streptomycin, bacitracin, chloroamphenicol, tyrothricin and the like; steroids having anti-inflammatory or other beneficial activity; antihistamines such as prophenpyridamine maleate and diphenhydramine hydrochloride; anesthetics such as benzocaine and lidocaine; antibacterials including iodine, nitrofurazone, sulfanylamide and derivatives, and benzalkonium chloride; fungicides such as undecylenic acid; and older therapeutic agents including coal tar, balsum Peru, ammoniated mercury, chrysarobin, ichthammol, sulfur and the like.

The ointment base of this invention is particularly suitable for use with medicaments which are soluble in propylene carbonate and propylene carbonate-cosolvent mixtures.

The ointment containing the medicaments can be prepared by conventional techniques. For example, the medicament can be dissolved in the propylene carbonate which can then be mixed with the other components. Alternatively, the medicament can be added directly to the ointment base. The amount of medicament to be incorporated in the ointment will, of course, depend upon the type of medicament and its intended use. The determination of suitable medicament concentrations is a routine matter fully within the conventional skill of the art. In general, therapeutically effective amounts of the medicament are incorporated in the ointment.

The ointment of this invention is particularly suitable for use with anti-inflammatory topical steroids represented by Formulas I, II and III.

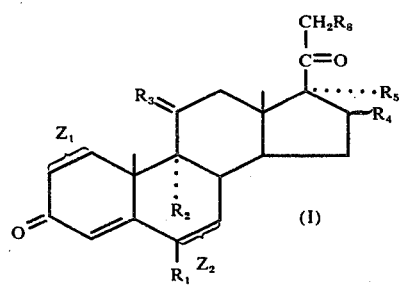

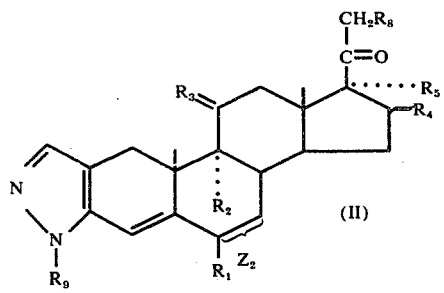

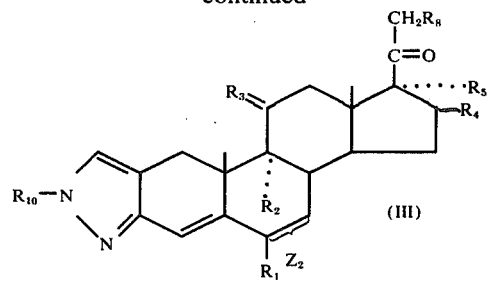

wherein
$R_1$ is hydrogen, methyl, fluoro, or chloro and when $Z_2$ is a single bond, $R_1$ can be either $\alpha$ or $\beta$ oriented;
$R_2$ is hydrogen, chloro, or fluoro;
$R_3$ is keto or

wherein $R_3'$ is hydrogen, hydroxy, chloro, or fluoro;
$R_4$ is hydrogen, methyl, hydroxy, or conventional hydrolyzable esters thereof;
$R_5$ is hydrogen, hydroxy, conventional hydrolyzable esters thereof, or when taken together with $R_4$;

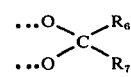

wherein
$R_6$ is hydrogen or alkyl of up to eight carbons, andd
$R_7$ is hydrogen, or alkyl or an aryl group of up to eight carbons;
$R_8$ is hydroxy, conventional hydrolyzable esters thereof, tetrahydropyranyloxy, tetrahydrofuranyloxy, 4'-(lower)alkoxytetrahydropyran-4'-yloxy, lower alkoxy, lower cycloalkoxy, lower cycloalkenyloxy, chloro, or fluoro;
$R_9$ and $R_{10}$ are hydrogen, methyl, phenyl, chlorophenyl, fluorophenyl, methyl phenyl, or methoxyphenyl (the substituted phenyls preferred being substituted in the para position);
$R_{11}$ and $R_{12}$ each is hydrogen, chloro, or fluoro;
$Z_1$ and $Z_2$ each is a single bond, double bond, or

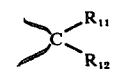

The terms "(lower)alkyl" and derivations thereof appearing in the above definitions and elsewhere in the instant specification denote alkyl groups having from one to six carbon atoms, inclusive, such as methyl, ethyl, propyl, isopropyl, butyl, isobutyl, t-butyl, pentyl, amyl, hexyl, and the like.

The term "conventional hydrolyzable ester" as used herein denotes those hydrolyzable ester groups conventionally employed in the steroid art, preferably those derived from hydrocarbon carboxylic acids or phosphoric acids and their salts. The term "hydrocarbon carboxylic acid" defines both substituted and unsubstituted hydrocarbon carboxylic acids. These acids can be completely saturated or possess varying degrees of unsaturation (including aromatic), can be of straight chain, branched chain, or cyclic structure, and preferably contain from one to 12 carbon atoms. In addition, they can be substituted by functional groups, for example, hydroxy, alkoxy containing up to six carbon atoms, acyloxy containing up to 12 carbon atoms, nitro, amino, halogeno, and the like, attached to the hydrocarbon backbone chain. Typical conventional hydrolyzable esters thus included within the scope of the term and the instant invention are acetate, propionate, butyrate, valerate, caproate, enanthate, caprylate, pelargonate, acrylate, undecenoate, phenoxyacetate, benzoate, phenylacetate, diphenylacetate, diethylacetate, trimethylacetate, t-butylacetate, trimethylhexanoate, methylneopentylacetate, cyclohexylacetate, cyclopentylpropionate, adamantoate, glycolate, methoxyacetate, hemisuccinate, hemiadipate, hemi-$\beta,\beta$-dimethylglutarate, acetoxyacetate, 2-chloro-4-nitrobenzoate, aminoacetate, diethylaminoacetate, piperidinoacetate, $\beta$-chloropropionate, trichloroacetate, $\beta$-chlorobutyrate, dihydrogen phosphate, dibenzyl phosphate, benzyl hydrogen phosphate, sodium benzyl phosphate, cyclohexylammonium benzyl phosphate, sodium phenyl phosphate, sodium ethyl phosphate, di-p-nitrobenzyl phosphate, sodium o-methoxyphenyl phosphate, cyclohexylammonium p-cyanobenzyl phosphate, sodium phenacyl phosphate, benzyl o-carbomethoxyphenyl phosphate, and the like.

By the term "aryl" are included aryl, aralkyl, and alkaryl groups, such as phenyl, p-chlorophenyl, p-methoxyphenyl, benzyl, phenethyl, tolyl, ethylphenyl, and the like. The wavy line ( $\mathcal{l}$ ) designates and includes both the alpha and beta configurations The above anti-inflammatory steroids have been previously disclosed in U.S. Pat. Nos. 3,365,446, 3,067,194, 3,364,203, 3,053,833 and 3,513,162, for example.

The above anti-inflammatory topical medicaments are thoroughly mixed with the base in therapeutically effective amounts. The particular concentration of the medicament in the base will vary depending upon the particular activity of the steroid used considered in conjunction with the condition and subject to be treated. In general, therapeutically effective amounts of these compounds can be as low as 0.00001 weight percent or lower, for example. For some uses, as high as 5 weight percent steroid or higher may be desired.

The ointment of this invention has been found to be unexpectedly superior to previously known ointments for use with known topical corticoids, for example, fluocinolone acetonide ($6\alpha,9\alpha$-difluoro-$11\beta,21$-dihydroxy-$16\alpha,17\alpha$-isopropylidenedioxypregna-1,4-diene-3,20-dione) and the corresponding 21-acetate ($6\alpha,9\alpha$-difluoro-$11\beta$-hydroxy-$16\alpha,17\alpha$-isopropylidenedioxy-21-acetoxypregna-1,4-diene-3,20-dione). In preliminary tests, these medicaments in the ointment of this invention have been observed to have several times greater activity in comparison to their activity in previously known ointments at the same concentration.

This invention is further illustrated by the following specific but non-limiting examples.

EXAMPLE 1

An ointment base having the following composition is prepared.

| Ingredients | Concentration, wt.% |
|---|---|
| Propylene glycol | 1.5 |
| Propylene carbonate | 3.5 |
| Lanolin | 4.0 |
| Petrolatum | 91.0 |

The propylene glycol and propylene carbonate are mixed together while heated to a temperature of 70° C. The petrolatum is heated to 65°–70° C, and lanolin is mixed therewith with stirring. The propylene glycol-propylene carbonate mixture is added to the latter mixture with stirring and the resulting mixture is cooled to room temperature with stirring.

The above procedure is repeated but 0.05 gm. of $6\alpha,9\alpha$-difluoro-$11\beta$-hydroxy-$16\alpha,17\alpha$-isopropylidenedioxy-21-acetoxypregna-1,4-diene-3,20-dione is dissolved in the propylene glycol and propylene carbonate mixture prior to its addition to the petrolatum-lanolin mixture.

EXAMPLE 2

An ointment base having the following composition is prepared.

| Ingredients | Concentration, wt.% |
|---|---|
| Propylene glycol | 1.5 |
| Propylene carbonate | 3.5 |
| Cholesterol | 3.0 |
| Stearyl alcohol | 3.0 |
| Arlacel 83[(a)] | 3.0 |
| Tween 80[(b)] | 2.0 |
| Petrolatum | 84.0 |

[(a)]Sorbitan sesquioleate
[(b)]Polyoxyethylene sorbitan monooleate

The propylene glycol and propylene carbonate are thoroughly mixed with heating. The cholesterol, stearyl alcohol, Arlacel 83, and Tween 80 are thoroughly mixed with heating. The petrolatum is heated to 65°–70° C, and the cholesterol and propylene carbonate containing mixtures, prepared above, are added sequentially thereto with stirring. The resulting mixture is then cooled to room temperature with stirring.

The above procedure is repeated but 0.05 gm. of $6\alpha,9\alpha$-difluoro-$11\beta$-hydroxy-$16\alpha,17\alpha$-isopropylidenedioxy-21-acetoxypregna-1,4-diene-3,20-dione is dissolved in the propylene glycol and propylene carbonate mixture prior to its addition to the petrolatum.

EXAMPLE 3

An ointment base having the following composition is prepared.

| Ingredients | Concentration, wt.% |
|---|---|
| Propylene glycol | 1.5 |
| Propylene carbonate | 3.5 |
| Arlacel 83 | 3.0 |
| Tween 80 | 2.0 |
| White petrolatum | 90.0 |

The propylene glycol and propylene carbonate are thoroughly mixed with heating. The petrolatum is heated to 65°–75° C, and Arlacel 83 and Tween 80 is added to this with stirring. Then the propylene glycol and propylene carbonate solution is added to the mixture, and the resulting mixture is then cooled to room temperature with stirring.

The above procedure is repeated but 0.06 gm. of 6α,9α-difluoro-11β-hydroxy-16α,17α-isopropylidenedioxy-21-acetoxypregna-1,4-diene-3,20-dione is dissolved in the propylene glycol and propylene carbonate solution prior to its addition to the petrolatum.

EXAMPLE 4

An ointment base having the following composition base is prepared.

| Ingredients | Concentration, wt.% |
|---|---|
| Propylene carbonate | 10 |
| Liquid petrolatum | 40 |
| Lanolin | 5 |
| Isopropyl myristate | 30 |
| Colloidal silica[a] | 15 |

[a]Cabosil or Quso.

The propylene carbonate and isopropyl myristate are thoroughly mixed with heating. The lanolin and petrolatum is added to this mixture with stirring. The colloidal silica is then carefully added to the mixture with stirring, and the mixture is cooled to room temperature while stirring.

The above procedure is repeated but 0.150 gm. of 6α,9α-difluoro-11β-hydroxy-16α,17α-isopropylidenedioxy-21-acetoxypregna-1,4-diene-3,20-dione is dissolved in the propylene carbonate and isopropyl myristate mixture prior to mixing it with lanolin and liquid petrolatum.

EXAMPLE 5

An ointment having the following composition is prepared.

| Ingredients | Concentration, wt.% |
|---|---|
| Propylene carbonate | 5 |
| Petrolatum | 63 |
| Span 60[a] | 5 |
| Tween 60[b] | 5 |
| Lanolin | 10 |
| Beeswax | 5 |
| Hard paraffin | 2 |
| Propylene glycol | 5 |

[a]Sorbitan monostearate
[b]Polyoxyethylene Sorbitan monostearate

The petrolatum, beeswax and hard paraffin are heated to 65°–70° C and mixed together with stirring. The Span 60, Tween 60 and lanolin are added to this mixture with stirring. A solution of propylene carbonate and propylene glycol is then prepared and added to the above mixture with stirring. The resulting mixture is then cooled to room temperature with stirring.

The above procedure is repeated but 0.075 gm. of 6α,9α-difluoro-11β-hydroxy-16α,17α-isopropylidenedioxy-21-acetoxypregna-1,4-diene-3,20-dione is dissolved in the propylene glycol and propylene carbonate mixture prior to its addition to the petrolatum mixture.

EXAMPLE 6

An ointment having the following composition is prepared.

| Ingredients | Concentration, wt.% |
|---|---|
| Propylene carbonate | 3 |
| Polysiloxane[a] | 30 |
| Propylene glycol | 2 |
| Arlacel 83 | 2 |
| Petrolatum | 63 |

[a]Dimethyl polysiloxane, viscosity 1000 centipoises

The petrolatum and polysiloxane are heated together to 65°–70° C and mixed with stirring. Lanolin and Arlacel 83 is added to this mixture. Propylene carbonate and propylene glycol are separately mixed together and added to the ointment matrix with stirring, and the resultant mixture is cooled to room temperature with stirring.

The above procedure is repeated but 0.045 gm. of 6α,9α-difluoro-11β-hydroxy-16α,17α-isopropylidenedioxy-21-acetoxypregna-1,4-diene-3,20-dione is dissolved in the propylene carbonate prior to its addition to the other ingredients.

EXAMPLE 7

Each of 0.01, 0.05, 0.1, 0.5 and 1.0 quantities of the following anti-inflammatory steroids, when mixed with 1000 gm. of each of the vehicles described in Examples 1–6, inclusive, provides an ointment which is effective for topical treatment of inflammation:

9α-fluoro-11β-trihydroxy-16β-methylpregna-1,4-diene-3,20-dione,
9α-fluoro-11β,21-dihydroxy-16β-methyl-17α-valeroxypregna-1,4-diene-3,20-dione,
17α,21-dihydroxypregn-4-ene-3,11,20-trione,
17α-hydroxy-21-acetoxypregn-4-ene-3,11,20-trione,
21-hydroxypregn-4-ene-3,20-dione,
21-acetoxypregn-4-ene-3,20-dione,
21-pivaloxyapregn-4-ene-3,20-dione,
9α-fluoro-11β,17α,21-trihydroxy-16α-methylpregna-1,4-diene-3,20-dione,
9α-fluoro-11β,17α,21-trihydroxy-16α-methylpregna-1,4-diene-3,20-dione-21-sodium phosphate,
6α,9α-difluoro-11β,21-dihydroxy-16α,17α-isopropylidenedioxypregna-1,4-diene-3,20-dione,
6α,9α-difluoro-11β-hydroxy-16α,17α-isopropylidenedioxy-21-acetoxypregna-1,4-diene-3,20-dione,
6α-methyl-9α-fluoro-11β,17α-dihydroxypregna-1,4-diene-3,20-dione,
6α-fluoro-11β,17α,21-trihydroxypregna-1,4-diene-3,20-dione,
6α-fluoro-11β,21-dihydroxy-16α,17α-isopropylidenedioxypregn-4-ene-3,20-dione,
6α-fluoro-11β,21-dihydroxy-16α,17α-isopropylidenedioxypregna-1,4-diene-3,20-dione,
11β,17α-dihydroxy-21-acetoxypregn-4-ene-3,20-dione,
6α-methyl-11β,17α,21-trihydroxypregna-1,4-diene-3,20-dione,
6α-methyl-11β,17α-dihydroxy-21-acetoxypregna-1,4-diene-3,20-dione,
6α-fluoro-11β,17α,21-trihydroxy-16α-methylpregna-1,4-diene-3,20-dione,
6α-fluoro-11β,17α-dihydroxy-16α-methyl-21-acetoxypregna-1,4-diene-3,20-dione,
6α-fluoro-11β,17α-dihydroxy-16α-methyl-21-valeroxypregna-1,4-diene-3,20-dione,
11β,17α,21-trihydroxypregna-1,4-diene-3,20-dione, 11β,17α-dihydroxy-21-acetoxypregna-1,4-diene-3.20-dione,
17α,21-dihydroxypregna-1,4-diene-3,11,20-trione,
17α-hydroxy-21-acetoxypregna-1,4-diene-3,11,20-trione,
9α-fluoro-11β,16α,17α,21-tetrahydroxypregna-1,4-diene-3,20-dione,
9α-fluoro-11β,16α,17α-trihydroxy-21-acetoxypregna-1,4-diene-3,20-dione,
9α-fluoro-11β,21-dihydroxy-16α,17α-isopropylidenedioxypregna-1,4-diene-3,20-dione,
6α-fluoro-9α,11β-dichloro-16α,17α-isopropylidenedioxy-21-hydroxypregna-1,4-diene-3,20-dione,
6α,9α-difluoro-11β,21-dihydroxy-16α-methyl-17α-valeroxypregna-1,4-diene-3,20-dione,
6α,9α-difluoro-11β,17α,21-trihydroxy-16α-methylpregna-1,4-diene-3,20-dione,
6α,7α-difluoromethylene-11β,17α,21-trihydroxy-pregn-4-ene-3,20-dione,
6α-fluoro-11β,21-dihydroxy-16α-methylpregna-1,4-diene-3,20-dione,
6α,9α-difluoro-11β-hydroxy-16α,17α-isopropylidenedioxy-21-chloropregna-1,4-diene-3,20-dione and
9α,11β-dichloro-6α,21-difluoro-16α,17α-isopropylidenedioxypregna-1,4-diene-3,20-dione.

We claim:
1. An ointment comprising an ointment base consisting essentially of
  a. from 0.5 to 30 weight percent propylene carbonate;
  b. from 30 to 99.5 weight percent petrolatum, polysiloxane having a viscosity of from 0.5 to 10⁶ centistokes, or mixtures thereof;
  c. compatible co-solvent, the concentration of which in combination with the propylene carbonate is from 0.5 to 70 weight percent;
  d. from 0 to 45 weight percent pharmaceutically acceptable surfactant;
  e. from 0 to 20 weight percent thickener; and
  f. from 0 to 25 weight percent penetrant
  in combination with a therapeutically effective amount of a propylene carbonate soluble medicament.
2. The ointment of claim 1 wherein the medicament is a topically active anti-inflammatory steroid.
3. The ointment of claim 2 wherein the steroid is
  a. a pregn-4-ene-3,20-dione having at each of positions C-1,2 and C-6,7, a single bond, double bond or group having the formula

wherein $R_{11}$ and $R_{12}$ each is hydrogen, chloro or fluoro; at position C-6, hydrogen, methyl, fluoro or chloro; at position C-9, hydrogen, chloro, or fluoro; at position C-11, keto or

wherein $R_3'$ is hydrogen, hydroxy, chloro or fluoro; at position C-16, hydrogen, methyl, hydroxy or conventional hydrolyzable esters thereof, at position C-17α, hydrogen, hydroxy, conventional hydrolyzable esters thereof, or when taken together with C-16α, a group having the formula

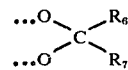

wherein $R_6$ is hydrogen or alkyl of up to 8 carbons, and $R_7$ is hydrogen, or alkyl or aryl having up to 8 carbons; and at position C-21, hydroxy, conventional hydrolyzable esters thereof, tetrahydropyranyloxy, tetrahydrofuranyloxy, 4'-(lower-)alkoxytetrahydropyran-4'-yloxy, lower alkoxy, lower cycloalkoxy, lower cycloalkenyloxy, chloro or fluoro; or
  b. a 2'-substituted-pregn-4-en-20-one-[3,2-c]pyrazole or a 1'-substituted-pregn-4-en-20-one-[3,2-c]-pyrazole having at the respective N-2' or N-1' positions, hydrogen, methyl, phenyl, chlorophenyl, fluorophenyl, methylphenyl, or methoxyphenyl, and having at C-6,7, a single bond, double bond or group having the formula

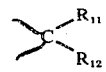

wherein $R_{11}$ and $R_{12}$ each is hydrogen, chloro or fluoro; at position C-6, hydrogen, methyl fluoro or chloro; at position C-9, hydrogen, chloro or fluoro; at position C-11, keto or

wherein $R_3'$ is hydrogen, hydroxy, chloro or fluoro; at position C-16, hydrogen, methyl, hydroxy or conventional hydrolyzable esters thereof, at position C-17α, hydrogen, hydroxy, conventional hydrolyzable esters thereof, or when taken together with C-16α, a group having the formula

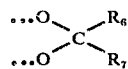

wherein $R_6$ is hydrogen or alkyl of up to 8 carbons, and $R_7$ is hydrogen, or alkyl or aryl having up to 8 carbons; and at position C-21, hydroxy, conventional hydrolyzable esters thereof, tetrahydropyranyloxy, tetrahydrofuranyloxy, 4'-(lower-)alkoxytetrahydropyran-4'-yloxy, lower alkoxy, lower cycloalkoxy, lower cycloalkenyloxy, chloro or fluoro.
4. The ointment of claim 3 wherein the steroid is 6α,9α-difluoro-11β-hydroxy-16α,17α-isopropylidenedioxy-21-acetoxypregna-1,4-diene-3,20-dione.
5. The ointment of claim 3 wherein the steroid is 6α,9α-difluoro-11β,21-dihydroxy-16α,17α-isopropylidenedioxypregna-1,4-diene-3,20-dione.
6. The ointment of claim 3 wherein the steroid is 6α-fluoro-9α,11β-dichloro-16α,17α-isopropylidenedioxy-21-hydroxypregna-1,4-diene-3,20-dione.
7. The ointment of claim 3 wherein the steroid is 9α,11β-dichloro-6α,21-difluoro-16α,17α-isopropylidenedioxypregna-1,4-diene-3,20-dione.

* * * * *